Figure 1:
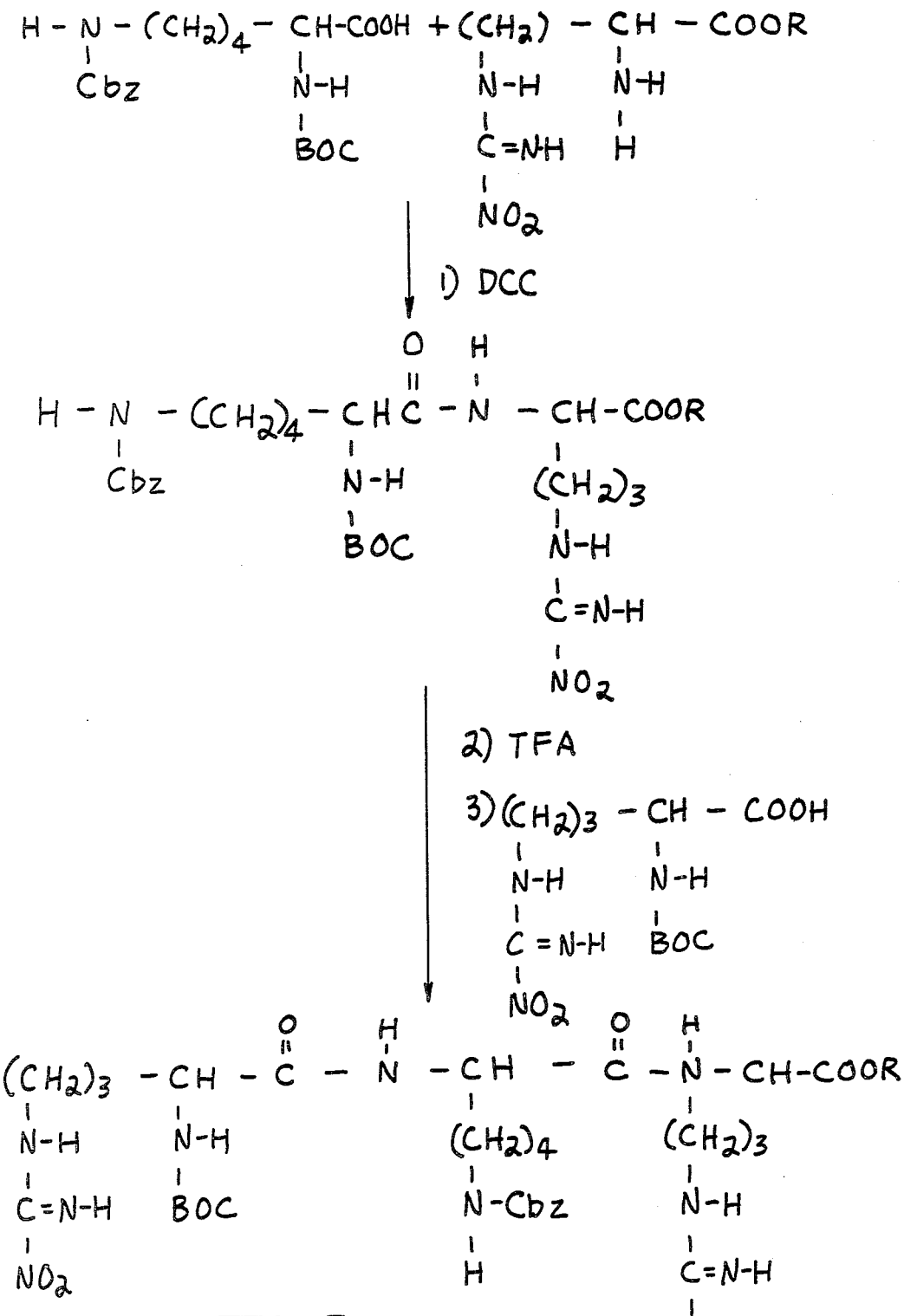
Figure 2:
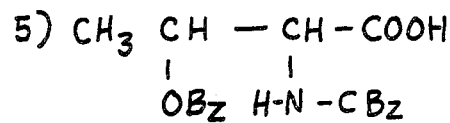
Figure 2:
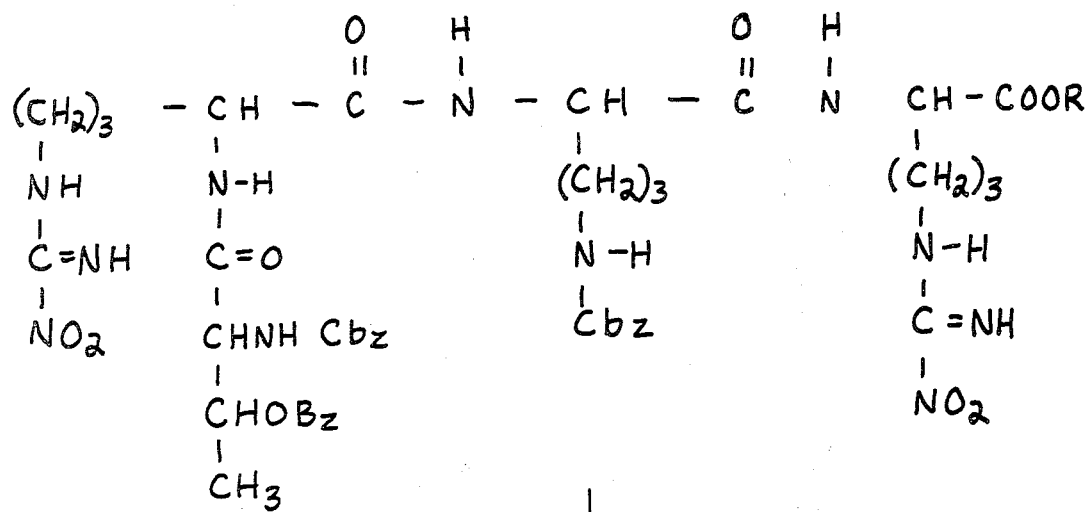
Figure 2:
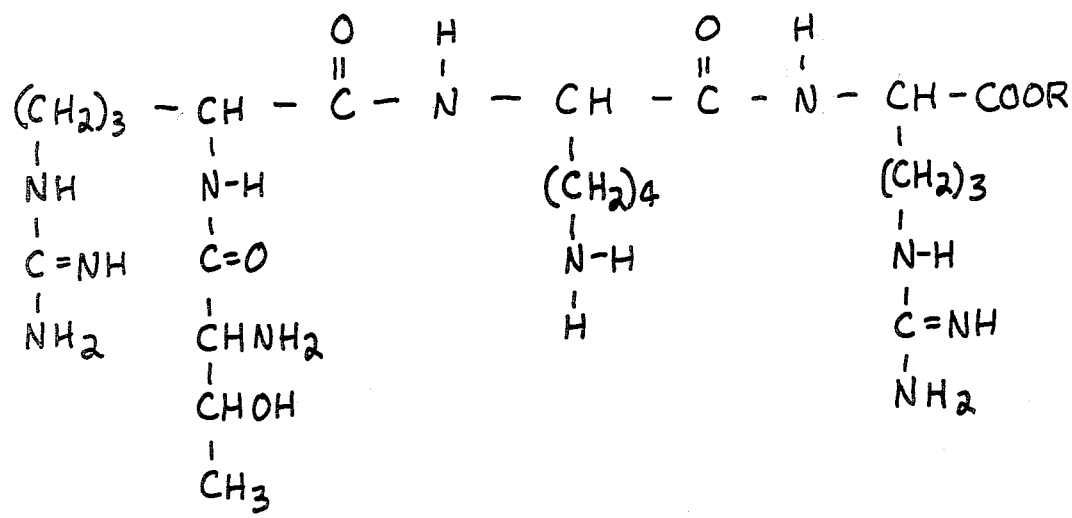

United States Patent [19]
Kent, Jr.

[11] 4,181,717
[45] Jan. 1, 1980

[54] OVULATION ENHANCING PEPTIDES

[75] Inventor: Harry A. Kent, Jr., Piscataway, N.J.

[73] Assignee: Research Corporation, New York, N.Y.

[21] Appl. No.: 940,451

[22] Filed: Sep. 7, 1978

[51] Int. Cl.² .................... A61K 37/00; C07C 103/52
[52] U.S. Cl. ............................ 424/177; 260/112.5 R
[58] Field of Search ................. 424/177; 260/112.5 R

[56] References Cited
PUBLICATIONS

G. R. Pettit, Synthetic Peptides I, p. 253.

*Primary Examiner*—Delbert R. Phillips
*Attorney, Agent, or Firm*—Cooper, Dunham, Clark, Griffin & Moran

[57] ABSTRACT

Polypeptides containing at least four amino acids are useful to enhance ovulation in mammals.

22 Claims, 2 Drawing Figures

OVULATION ENHANCING PEPTIDES

The invention described herein was made in the course of work under a grant or award from the Department of Health, Education and Welfare.

BACKGROUND OF THE INVENTION

This invention is concerned with novel polypeptides, particularly polypeptides containing at least four and up to about eight amino acids, as well as their pharmacologically acceptable derivatives and salts. These compounds are useful both orally and parenterally to enhance ovulation.

The principal class of compounds now utilized to enhance ovulation for animals, including humans, are steroidal in nature. The use of such compounds is associated with a certain degree of well recognized risks of side effects such as variations in blood pressure and alterations in metabolism of both lipids and carbohydrates, as well as a variety of other symptoms, including headache, fluid and salt retention, bloating, and nausea.

Accordingly, the art has long been interested in finding suitable substitutes for steroidal ovulation stimulators.

THE INVENTION

Novel polypeptides have now been found which are useful for this purpose. These peptides and certain derivatives and salts, when administered orally or parenterally to animals, are useful for the stimulation of ovulation.

For convenience, the standard abbreviations for amino acids will hereinafter be used:
Thr—threonine
Arg—arginine
Lys—lysine
Ser—serine
Orn—ornithine
His—histidine The products of this invention are polypeptides containing at least four and up to eight amino acids, the four amino acids being:
1. selected from the group consisting of threonine, serine, arginine, lysine, ornithine and histidine;
2. formed in a tetrapeptide unit, the amino terminus of which is the amino acid threonine or serine, said threonine or serine being formed in a peptide bond through its carboxyl group to the α-amino group of arginine or lysine;
3. the remaining two amino acids in said tetrapeptide unit being selected from the group consisting of arginine, lysine, ornithine and histidine;

and pharmacologically acceptable salts thereof.

The polypeptides of this invention form a relatively large but finite number of compounds which are:

H—Thr—Arg—Arg—Arg—OH
H—Thr—Arg—Arg—Lys—OH
H—Thr—Arg—Lys—Arg—OH
H—Ser—Arg—Arg—Arg—OH
H—Ser—Arg—Arg—Lys—OH
H—Ser—Arg—Lys—Arg—OH
H—Thr—Lys—Lys—Lys—OH
H—Thr—Lys—Lys—Arg—OH
H—Thr—Lys—Arg—Lys—OH
H—Ser—Lys—Lys—Lys—OH
H—Ser—Lys—Lys—Arg—OH
H—Ser—Lys—Arg—Lys—OH
H—Thr—Arg—Arg—Orn—OH
H—Thr—Arg—Lys—Orn—OH
H—Ser—Arg—Arg—Orn—OH
H—Ser—Arg—Lys—Orn—OH
H—Thr—Lys—Lys—Orn—OH
H—Thr—Lys—Arg—Orn—OH
H—Ser—Lys—Arg—Orn—OH
H—Ser—Lys—Lys—Orn—OH
H—Thr—Arg—Arg—His—OH
H—Thr—Arg—Lys—His—OH
H—Ser—Arg—Arg—His—OH
H—Ser—Arg—Lys—His—OH
H—Thr—Lys—Lys—His—OH
H—Thr—Lys—Arg—His—OH
H—Ser—Lys—Arg—His—OH
H—Ser—Lys—Lys—His—OH
H—Thr—Arg—Orn—Arg—OH
H—Thr—Arg—Orn—Lys—OH
H—Ser—Arg—Orn—Arg—OH
H—Ser—Arg—Orn—Lys—OH
H—Thr—Lys—Orn—Lys—OH
H—Thr—Lys—Orn—Arg—OH
H—Ser—Lys—Orn—Arg—OH
H—Ser—Lys—Orn—Lys—OH
H—Thr—Arg—His—Arg—OH
H—Thr—Arg—His—Lys—OH
H—Ser—Arg—His—Arg—OH
H—Ser—Arg—His—Lys—OH
H—Thr—Lys—His—Lys—OH
H—Thr—Lys—His—Arg—OH
H—Ser—Lys—His—Arg—OH
H—Ser—Lys—His—Lys—OH
H—Thr—Arg—Orn—His—OH
H—Thr—Arg—His—Orn—OH
H—Thr—Lys—Orn—His—OH
H—Thr—Lys—His—Orn—OH
H—Ser—Arg—Orn—His—OH
H—Ser—Arg—His—Orn—OH
H—Ser—Lys—Orn—His—OH
H—Ser—Lys—His—Orn—OH

Useful derivatives of the above mentioned tetrapeptides can be prepared by standard, well known chemical procedures. Most of these derivatives are prepared by reactions involving active hydrogens on, for example, free hydroxyl, amino, or carboxyl groups. For example, free hydroxyl, amino or guanidino nitrogens can be acylated with acyl groups containing up to about eighteen carbon atoms. Such modifications, especially when the acyl group contains ten or more carbon atoms, increases the lipid solubility of the compound and facilitates transport across cell barriers. The arginine moiety may be nitrated.

It is also useful to acylate a free hydroxyl or amino group with another amino acid. Thus the hydroxyl group on Thr or Ser; or the guanidino group on Arg; or the epsilon amino group on Lys can be derivatized with another amino acid such as glycine, phenylalanine, lysine, etc. This procedure is especially useful when the compound is to be administered orally, since the presence of the additional amino acid helps to protect the basic unit against attack by proteolytic enzymes of the digestive system.

The carboxyl group on the carboxyl terminal of the basic unit, or the amino group on the amino terminal of the basic unit may also serve as a reaction site for the addition of amino acids to extend the basic tetrapeptide unit to form peptides containing up to about eight amino acids. The unit might be repeated by combination of the carboxyl group of the lysine terminus of one tetrapeptide with the epsilon amino group on the lysine terminus of another identical tetrapeptide.

The terminal amino group might also be combined with the carboxyl group of cysteine. Oxidation of the resulting pentapeptide forms a nonapeptide dimer linked through cystine.

Hydrophilicity may be increased by derivatizing free hydroxyl groups with saccharides, particularly monosaccharides such as glucose, galactose, mannose and the like in hemiacetal formation.

Free carboxyl groups can be stabilized by conversion to amides or esters.

The reactions employed in the formation of these various derivatives are well known.

A particular advantage arising from the amphoteric nature of the peptides of this invention is that they can be utilized in the form of pharmacologically acceptable salts. These salts have the advantage of increased water solubility, and are particularly useful for parenteral administration. Of the metallic salts, the alkali and alkaline earth metal salts are preferred. The sodium salts are especially preferred because of their ease of preparation.

The acids which may be used to prepare the pharmacologically acceptable acid addition salts of this invention are those containing non-toxic anions and include, for example, hydrochloric, sulfuric, phosphoric, acetic, lactic, citric, tartaric, oxalic, succinic, maleic, gluconic, saccharic, and the like acids.

While it is generally preferred that the additional amino acids joined to the basic peptide unit be selected from the six amino acids listed above, or cysteine, it is not essential that they be so selected. Any of the known amino acids can be selected.

The preferred amino acids for all of the peptides used in this invention are the naturally occurring L-amino acids.

The most generally preferred basic unit tetrapeptides from the point of view of activity and preparative costs, are those in which the amino terminal amino acid is Thr or Ser, the next adjacent amino acid is Arg or Lys, and the final two amino acids are also Arg and Lys.

The products of this invention may be administered alone but will generally be administered with pharmaceutically acceptable, non-toxic carriers, the proportions of which are determined by the suitability and chemical nature of the particular carrier, the chosen route of administration, and standard pharmaceutical practice. For example, they may be administered orally in the form of tablets or capsules containing such excipients as starch, milk sugar, certain types of clay, etc. They may be enteric coated so as to be more resistant to the acid and digestive enzymes of the stomach. For intravenous and intramuscular administration, they may be used in the form of a sterile solution containing other solutes, for example, enough saline or glucose to make the solution isotonic. They may be administered in an oil vehicle such as sesame oil.

The products of this invention are useful mammalian therapeutic agents. The physician or veterinarian will determine the dosage which will be most suitable. It may vary from patient to patient depending on the factors which are readily evaluated by those skilled in the art.

Dosage units containing from about 0.15 to 0.5 mg. are useful. A typical regimen for subcutaneous administration for an average sized woman is about 0.2 mg. per day. It may vary appreciably with oral administration since some of the active material may be hydrolyzed in the intestinal tract. However, as indicated above, the basic tetrapeptide unit may also be protected against premature hydrolysis by the formation of derivatives, particularly peptides containing additional amino acids.

A particular advantage of the products of this invention is that because of their relatively low molecular weight, there is no danger of an immune response.

The peptides of this invention can be synthesized by any of a wide variety of techniques now available for the synthesis of simple and complex polypeptides and even relatively low molecular weight proteins. In general, these techniques involve stepwise synthesis by successive additions of amino acids to produce progressively larger molecules. The amino acids are linked together by condensation between the carboxyl group of one amino acid and the amino group of another amino acid to form a peptide bond. In order to control these reactions, it is necessary to block the amino group of the one acid and the carboxyl group of the other. Necessarily, the blocking groups must be easily removed. The whole series of reactions must take place without causing racemization of the products.

A large number of procedures have been devised by the art for the synthesis of polypeptides and a wide variety of blocking agents are known. Most of these procedures are applicable to the synthesis of the polypeptides of this invention. No useful purpose would be served by describing the application of all of them.

Two of the procedures which may be used are the Merrifield technique and the N-carboxyl anhydride technique. In the former, an amino acid is first bound to a resin particle, as by an ester bond and the peptide is generated in a stepwise manner by successive additions of protected amino acids to the growing chain. In the latter, an N-carboxyl amino acid anhydride is reacted with the amino group of a second amino acid or peptide under conditions such that the only amino group present in appreciable concentration in reactive form during the course of the reaction is the amino group which is to participate in the reaction. This control is effected by selection of concentration, temperature, time and hydrogen ion concentration. The coupling reaction normally takes place under alkaline conditions, usually at a pH of from about 8.5 to 11. The intermediate carbamate is then decarboxylated by lowering the pH to from about 3 to 5. The product formed may be reacted with another N-carboxy amino acid anhydride without isolation and under substantially the same conditions. The process affords a very rapid method for the production of polypeptides.

Salts of the peptides are prepared by conventional procedures, for example by titration with aqueous acid or base.

The synthesis illustrated in the Figures shows one of the many methods that are available to synthesize the products of this invention. In the equations, the standard abbreviations normally employed in this art are utilized. Thus:

BOC is t-butoxy
DCC is dicyclohexylcarbodiimide
Cbz is carbobenzoxy
TFA is trifluoro acetic acid
R is the resin
Bz is benzyl The synthesis illustrated is applicable to the preparation of all of the tetrapeptides listed above. While the synthesis shows the use of Lys, Arg and Thr, it is also applicable to the preparation of products containing Ser, Orn and His. The imino group in His is protected. This protecting group can be removed by catalytic hydrogenation. Orn is similar to Lys and can be treated in substantially the same manner. Ser is similar to Thr and can also be treated in exactly the same manner.

Example 1 shows the process as applied to the preparation of a number of illustrative tetrapeptides of the invention.

It should be understood, however, that the process is illustrative and not limiting since, as indicated above, any of a large number of known peptide syntheses are applicable to the preparation of the compounds of this invention.

For the preparation of peptides containing more than four amino acids, the illustrated process is easily utilized at either end of the tetrapeptide. For example, the amino acid linked to the resin could be leucine. The product produced would then be:

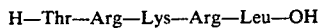
H—Thr—Arg—Lys—Arg—Leu—OH

Alternative, the chain could be lengthened from the amino terminal by the addition of an amino acid such as alanine or even a peptide such as Lys—Arg.

The compounds of this invention are useful in mammalian species to enhance ovulation.

In one study carried out with hamsters utilizing H—Thr—Arg—Lys—Arg—OH diacetate, each of six animals was injected subcutaneously at various dosage levels as indicated in the Table for each of the four days of the estrous cycle. On the fifth day, the animals were sacrificed, the left and right ovaries and oviducts of each animal collected, sectioned, stained, and the ova counted. The figures given in the second column are the mean numbers of ova for six animals at each dosage level. In a control group of 20 animals which were not treated with the ovulation enhancing compound, the mean number of ova counted under similar conditions was 11.3.

TABLE

| DOSE μgm/100 gm/day | Number of OVA |
|---|---|
| 0.10 | 13.7 |
| 0.30 | 14.1 |
| 3.00 | 15.5 |
| 30.00 | 15.6 |

H—Thr—Arg—Lys—Arg—OH, the first product of this invention which was isolated, was initially found as a by-product in the synthesis of H—Thr—Pro—Arg—Lys—OH, a contraceptive tetrapeptide by the Merrifield technique.

The following examples are given by way of illustration only.

EXAMPLE I

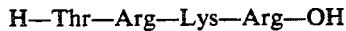
H—Thr—Arg—Lys—Arg—OH

This preparation is illustrated in the Figures, and can be easily followed by reference to the formulae and equations therein.

Nitro-Arg, 13.8 mmoles are reacted with 10 g. of chloromethyl-resin (polystyrene divinyl benzene chloromethyl resin 2.2 mmoles of chloride per gram of resin) in a mixture of triethylamine, 12.4 mmoles, and 30 ml. ethanol for 24 hours at 80° C. with constant magnetic stirring. The resin is then thoroughly washed with acetic acid, then with absolute ethanol, water with increasing concentration of ethanol, finally with absolute ethanol followed by methanol and methylene chloride. The resin is dried in vacuo to constant weight. 1.1 g. of resin representing 0.45 mmoles of nitro Arg are placed in the Merrifield solid phase vessel secured onto a clamp to the shaft of a 180° reversible stroke motor. All manipulations henceforth take place at room temperature with 180° rocking motion such that the resin is constantly agitated.

$N^\epsilon$-Cbz-$N^\alpha$-t-BOC-Lys, 1.35 mmoles in 15 ml of methylene chloride is then coupled to the $N^\alpha$ of nitro Arg with 1.35 mmoles of DCC for two hours with continuous shaking. The resin is washed with ethanol, chloroform and methylene chloride, 15 ml. of each 3 times, respectively. The t-BOC group is removed from the Lys with 50% trifluoroacetic acid in methylene chloride, washed and neutralized with triethylamine. In a similar manner, $N^\alpha$-t-BOC-nitro Arg 1.35 mmoles is coupled to the free amino group of the dipeptide, deprotected, neutralized and 1.35 mmoles of $N^\alpha$-Cbz-O-benzyl threonine is then coupled to the deprotected $N^\alpha$ of the nitro Arg group. Thus the steps of deprotection (cleavage of the t-BOC alone) with TFA, washing, neutralization with triethylamine, washing and coupling with DCC is repeated for each amino acid residue in an identical manner.

30 mg. of the tetrapeptide resin are hydrolyzed with 6 N hydrochloride acid in dioxane for 18 hours and the product assayed on the amino acid analyzer. It yields a ratio of Thr 1, Lys 1, Arg 2. The tetrapeptide is cleaved off the resin with hydrogen bromide in TFA at room temperature for 1½ hours. It is then dried in vacuo, washed twice with water and lyophilized. It is then taken up in 10 ml. of methanol containing 10% acetic acid. This is then exposed to catalytic hydrogenation with twice its weight (350 mg.) of palladium on barium sulfate in a hydrogen atmosphere at 60 poundsa per square inch pressure with continuous shaking for 24 hours at which time no nitro Arg is detected at 271 mμ, the peak of absorption. An aliquot is again hydrolyzed with 6 N HCl in water and assayed. This yields a comparable figure for Thr, Lys, and Arg.

The tetrapeptide which is in the form of the diacetate salt is then converted to the sodium salt by the addition of three equivalents of sodium hydroxide.

The final yield is about 65%.

The process is repeated to form the tetrapeptide with all amino acids in the D-form. It is repeated twice with Ser in place of Thr. Both all L- and all D-forms are prepared.

The following compounds are similarly prepared.

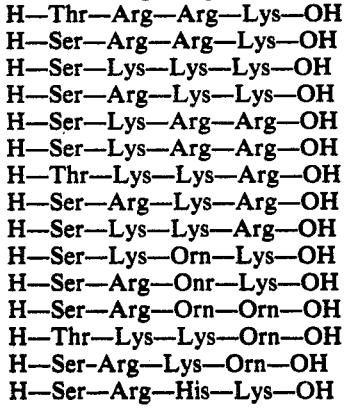
H—Thr—Arg—Arg—Lys—OH
H—Ser—Arg—Arg—Lys—OH
H—Ser—Lys—Lys—Lys—OH
H—Ser—Arg—Lys—Lys—OH
H—Ser—Lys—Arg—Arg—OH
H—Ser—Lys—Arg—Arg—OH
H—Thr—Lys—Lys—Arg—OH
H—Ser—Arg—Lys—Arg—OH
H—Ser—Lys—Lys—Arg—OH
H—Ser—Lys—Orn—Lys—OH
H—Ser—Arg—Onr—Lys—OH
H—Ser—Arg—Orn—Orn—OH
H—Thr—Lys—Lys—Orn—OH
H—Ser-Arg—Lys—Orn—OH
H—Ser—Arg—His—Lys—OH H—Thr—Arg—Lys—His—OH
H—Thr—Arg—Arg—Orn—OH
H—Ser—Arg—Arg—Orn—OH
H—Thr—Arg—Lys—Orn—OH
H—Thr—Arg—Arg—His—OH
H—Thr—Lys—Arg—His—OH
H—Thr—Lys—Lys—His—OH
H—Ser—Arg—Lys—His—OH
H—Thr—Arg—His—Orn—OH
H—Thr—Lys—His—Orn—OH

EXAMPLE II

STEAROYL—H—Thr—Arg—Lys—Arg—OH

The t-BOC group of 0.5 mmoles of O—Bz—N—t—BOC—Thr—nitro—Arg—N$^\epsilon$—Cbz—Lys—nitro—Arg—OH prepared by the procedures of Example I on 1.4 gm. of resin is cleaved with TFA as described above. The resulting product is coupled with 1.5 mmole of stearic acid using DCL, 1.5 mmole in chloroform-dimethylformamide. The ester is cleaved from the resin as described above with HBr in TFA. The resulting products are hydrogenated with H$_2$/Pd/BaSO$_4$ to reduce the nitro groups, cleave the carbobenzoxy groups and yield the desired product. Similar results are obtained with other fatty acids including acetic, propionic, lauric, myristic and palmitic.

What is claimed is:

1. Polypeptides containing four amino acids, which are:
    1. selected from the group consisting of threonine, serine, arginine, lysine, ornithine and histidine;
    2. formed in a tetrapeptide unit, the amino terminus of which is the amino acid threonine or serine, said threonine or serine being formed in a peptide bond through its carboxyl group to the α-amino group of arginine or lysine;
    3. the remaining two amino acids in said tetrapeptide unit being selected from the group consisting of arginine, lysine, ornithine and histidine;

and pharmacologically acceptable salts thereof.

2. Polypeptides of claim 1 wherein the amino terminus is threonine joined through its carboxyl group to the α-amino group of arginine, and the remaining two amino acids are selected from the group consisting of arginine and lysine, and the pharmacologically acceptable salts thereof.

3. H—Thr—Arg—Arg—Arg—OH and the pharmacologically acceptable salts thereof.

4. H—Thr—Arg—Arg—Lys—OH and the pharmacologically acceptable salts thereof.

5. H—Thr—Arg—Lys—Lys—OH and the pharmacologically acceptable salts thereof.

6. H—Thr—Arg—Lys—Arg—OH and the pharmacologically acceptable salts thereof.

7. Polypeptides of claim 1 wherein the amino terminus is serine joined through its carboxyl group to the α-amino group of arginine, and the remaining two amino acids are selected from the group consisting of arginine and lysine, and the pharmacologically acceptable salts thereof.

8. H—Ser—Arg—Arg—Arg—OH and the pharmacologically acceptable salts thereof.

9. H—Ser—Arg—Arg—Lys—OH and the pharmacologically acceptable salts thereof.

10. H—Ser—Arg—Lys—Lys—OH and the pharmacologically acceptable salts thereof.

11. H—Ser—Arg—Lys—Arg—OH and the pharmacologically acceptable salts thereof.

12. A composition comprising a pharmaceutically acceptable carrier and at least one compound selected from the group consisting of polypeptides containing four amino acids, which are:
    1. selected from the group consisting of threonine, serine, arginine, lysine, ornithine and histidine;
    2. formed in a tetrapeptide unit, the amino terminus of which is the amino acid threonine or serine, said threonine or serine being formed in a peptide bond through its carboxyl group to the α-amino group of arginine or lysine;
    3. the remaining two amino acids in said tetrapeptide unit being selected from the group consisting of arginine, lysine, ornithine and histidine;

and pharmacologically acceptable salts thereof.

13. A composition of claim 12 containing polypeptides wherein the amino terminus is threonine joined through its carboxyl group to the α-amino group of arginine, and the remaining two amino acids are selected from the group consisting of arginine and lysine, and the pharmacologically acceptable salts thereof.

14. A composition comprising a pharmaceutically acceptable carrier and at least one compound selected from the group consisting of H—Thr—Arg—Arg—Arg—OH and the pharmacologically acceptable salts thereof.

15. A composition comprising a pharmaceutically acceptable carrier and at least one compound selected from the group consisting of H—Thr—Arg—Arg—Arg—Lys—OH and the pharmacologically acceptable salts thereof.

16. A composition comprising a pharmaceutically acceptable carrier and at least one compound selected from the group consisting of H—Thr—Arg—Lys—Lys—OH and the pharmacologically acceptable salts thereof.

17. A composition comprising a pharmaceutically acceptable carrier and at least one compound selected from the group consisting of H—Thr—Arg—Lys—Arg—OH and the pharmacologically acceptable salts thereof.

18. A composition of claim 12 containing polypeptides wherein the amino terminus is serine joined through its carboxyl group to the α-amino group of arginine, and the remaining two amino acids are selected from the group consisting of arginine and lysine, and the pharmacologically acceptable salts thereof.

19. A composition comprising a pharmaceutically acceptable carrier and at least one compound selected from the group consisting of H—Ser—Arg—Arg—Arg—OH and the pharmacologically acceptable salts thereof.

20. A composition comprising a pharmaceutically acceptable carrier and at least one compound selected from the group consisting of H—Ser—Arg—Arg—Lys—OH and the pharmacologically acceptable salts thereof.

21. A composition comprising a pharmaceutically acceptable carrier and at least one compound selected from the group consisting of H—Ser—Arg—Lys—Lys—OH and the pharmacologically acceptable salts thereof.

22. A composition comprising a pharmaceutically acceptable carrier and at least one compound selected from the group consisting of H—Ser—Arg—Lys—Arg—OH and the pharmacologically acceptable salts thereof.